(12) United States Patent
Zhong et al.

(10) Patent No.: US 10,309,834 B2
(45) Date of Patent: Jun. 4, 2019

(54) CALIBRATING METHOD AND DEVICE FOR BROAD-BAND ACHROMATIC COMPOSITE WAVE PLATE AND CORRESPONDING MEASUREMENT SYSTEM

(71) Applicant: RAINTREE SCIENTIFIC INSTRUMENTS (SHANGHAI) CORPORATION, Shanghai (CN)

(72) Inventors: Fengjiao Zhong, Shanghai (CN); Haijun Gao, Shanghai (CN); Jiangtao Dang, Shanghai (CN)

(73) Assignee: Raintree Scientific Instruments (Shanghai) Corporation, Shanghai (CN)

( * ) Notice: Subject to any disclaimer, the term of this patent is extended or adjusted under 35 U.S.C. 154(b) by 25 days.

(21) Appl. No.: 15/570,557

(22) PCT Filed: Apr. 14, 2016

(86) PCT No.: PCT/CN2016/079225
§ 371 (c)(1),
(2) Date: Oct. 30, 2017

(87) PCT Pub. No.: WO2016/173399
PCT Pub. Date: Nov. 3, 2016

(65) Prior Publication Data
US 2018/0283951 A1    Oct. 4, 2018

(30) Foreign Application Priority Data

Apr. 30, 2015 (CN) .......................... 2015 1 0218243

(51) Int. Cl.
*G01J 4/04* (2006.01)
*G01M 11/02* (2006.01)

(52) U.S. Cl.
CPC .............. *G01J 4/04* (2013.01); *G01M 11/02* (2013.01)

(58) Field of Classification Search
CPC .................................. G01J 4/04; G01M 11/02
See application file for complete search history.

(56) References Cited

U.S. PATENT DOCUMENTS

2011/0032502 A1   2/2011  Nomura
2015/0029507 A1   1/2015  Liu et al.

FOREIGN PATENT DOCUMENTS

| CN | 102393555 A | 3/2012 |
| CN | 103424839 A | 3/2012 |
| CN | 102539119 A | 7/2012 |
| CN | 103472556 A | 12/2013 |
| CN | 103837476 A | 6/2014 |

OTHER PUBLICATIONS

Gaozeng Cui et al. ("Calibration of the MgF2 biplate compensator using a straight-through ellipsometer", IEEE Computer Society, (2013) pp. 731-735) (Year: 2013).*
International Search Report, dated Jun. 30, 2016 (PCT/CN2016/079225).

* cited by examiner

*Primary Examiner* — Hina F Ayub
(74) *Attorney, Agent, or Firm* — Robert L. Stearns; Dickinson Wright, PLLC

(57) ABSTRACT

The present disclosure discloses a calibrating method, apparatus, and corresponding measurement system for a composite waveplate. The calibrating method comprises: A. determining a first matrix characterizing the composite waveplate, the first matrix including at least one unknown number; B. determining a theoretical relationship between a light intensity and an alignment angle offset value of the composite waveplate based on the first matrix; and C. calibrating based on the theoretical relationship between a light intensity and an alignment angle offset value of the composite waveplate determined in step (B) and actually measured light intensity data to obtain a second matrix that may characterize the composite waveplate and does not contain the unknown number. The technical solution of the present disclosure may greatly reduce the amount of unknown numbers when calibrating a composite waveplate or a measuring system, thereby lowering the difficulty of calibration and improving the precision of calibration.

17 Claims, 2 Drawing Sheets

CALIBRATING METHOD AND DEVICE FOR BROAD-BAND ACHROMATIC COMPOSITE WAVE PLATE AND CORRESPONDING MEASUREMENT SYSTEM

CROSS-REFERENCE TO RELATED APPLICATIONS

This U.S. Utility Patent Application claims priority to PCT Application No. PCT/CN2016/079225, filed Apr. 14, 2016, which claims priority to Chinese patent application No. 201510218243.7, filed Apr. 30, 2015, the entirety of which is incorporated in the present disclosure by reference.

BACKGROUND

1. Technical Field

The present disclosure relates to the technical field of polarized optical detection, and more specifically to a broad-band achromatic composite waveplate calibrating method for Muller matrix measurement.

2. Related Art

Muller matrix measurement is one of important approaches for polarization detection. The Muller matrix measurement as a 4×4 matrix describes polarization effects and characteristics of optical devices and materials. The Muller matrix contains almost all polarization information of measured materials and are widely applied to various fields such as material, biology, and semiconductor. Particularly in critical dimension measurement (OCD) in semiconductor processing, the Muller matrix is an important technology to overcome the defects of the existing OCD measurement technologies and it is the fundamental technology for the next generation process OCD measurement.

A Muller matrix measurement system generally comprises the following main components: a polarization generator, a measured sample, a polarization analyzer, and a detector, wherein the polarization generator, which has a similar structure to a polarization analyzer, is generally combined by a polarization device and a phase compensation device, the phase compensation device being generally a waveplate, a photoelastic modulator, or a liquid crystal modulator, etc. Generally, the phase compensation device in Mueller matrix measurement is required to be capable of working in a very broad waveband, and the generated phase compensation may be limited in a small range within a broader waveband scope, i.e., achromatic, wherein what is exploited widely is an achromatic composite waveplate, which is featured by a compact dimension, a simple structure, and an easily adjusted light path, etc.

An achromatic composite waveplate is generally comprised of two or more single waveplates. The waveplate, as a common optical element in the fields of optical instrument design and optical measurement, is also referred to as an optical phase delay plate, which includes an additional phase difference to the two vertical components of a polarized light, thereby changing or checking a polarized state of a light wave. A waveplate is usually made of a uniaxial or biaxial crystal material. Materials used for manufacturing waveplates generally include: Quartz, magnesium fluoride, mica, gypsum, and sapphire, etc. A waveplate comprising a single waveplate is referred to as a single waveplate, and a waveplate comprising two or more crystal plates is referred to as a composite waveplate.

What is practically applied is usually a composite waveplate made of two single waveplates of two materials, whose optical axes are perpendicular to each other. For special use demands, a more complex achromatic composite waveplate may also be designed and manufactured. Such composite waveplates are made by a combination of a plurality of single waveplates of the same material or of different materials, and the included angle between the optical axes of respective single plates is an optimized angle value. These composite waveplates may obtain a good achromatic result, and such performance of improving waveplate precision and eliminating the chromatic aberration of the waveplates per se cannot be attained by a single waveplate. Therefore, composite waveplates are widely applied in optical instrument design and optical measurement.

In practical applications, for example, in Mueller matrix measurement, corresponding achromatic composite waveplates are designed for specific requirements. To ensure measurement precision of the instrument, it is required that the optical axes of respective single waveplates forming the composite waveplate are strictly aligned according to a designed angle. However, in actual manufacturing processes, neither the approach of manual alignment by experience nor the approach of alignment by light extinction may ensure the alignment precision, and the alignment angle is always offset from the designed angle. As a result, the polarization performance (i.e., the Mueller matrix of the composite waveplate) of the manufactured achromatic composite waveplate has gaps from the designed ideal Mueller matrix, which should be calibrated precisely in instrument measurement.

Some existing methods for calibrating the optical elements in a Mueller matrix measurement system do not separately consider the issue of calibrating the waveplate when the optical axes of the composite waveplate are not aligned. It is generally believed that the composite waveplate is an ideal waveplate, such that only its phase delay amount is calibrated; however, in actual applications, particularly in the Mueller matrix measurement system, the impact caused by misalignment of optical axes must be considered.

Therefore, a high-speed high-precision calibrating method for a composite waveplate is urgently needed.

SUMMARY

Based on the considerations above, a high-speed high-precision calibrating method and apparatus for a composite waveplate are urgently needed, which will be very advantageous.

An aspect of the present disclosure discloses a calibrating method for a composite waveplate, comprising: A. determining a first matrix characterizing the composite waveplate, the first matrix including at least one unknown number; B. determining a theoretical relationship between a light intensity and an alignment angle offset value of the composite waveplate based on the first matrix; C. calibrating based on the theoretical relationship between a light intensity and an alignment angle offset value of the composite waveplate determined in step (B) and actually measured light intensity data to obtain a second matrix that may characterize the composite waveplate and does not contain the unknown number.

Preferably, the at least one unknown number includes the alignment angle offset value.

Preferably, the step A further comprises: determining the first matrix based on a third matrix characterizing a single waveplate in the composite waveplate and a coordinate transformation matrix determined by an alignment angle design value and the alignment angle offset value.

Preferably, the step A further comprises: determining the third matrix based on characteristic parameters of the single waveplate, wherein the characteristic parameters include at least one of the following: number of the single waveplates; materials of the respective single waveplates; and thickness of the respective single waveplates;

Preferably, the step B further comprises: constructing a function relationship between matrix elements and the alignment angle offset value in the first matrix, such that each matrix element corresponds to the alignment angle offset value.

Preferably, the step C further comprises: determining the alignment angle offset value based on at least one wavelength to further determine an unknown matrix element in the first matrix so as to determine the second matrix.

Another aspect of the present disclosure discloses a calibrating apparatus for a composite waveplate, comprising: a detecting unit configured to receive or detect a measured light intensity; a processing unit configured to: determine a first matrix characterizing the composite waveplate, the first matrix including at least one unknown number; determine a theoretical relationship between the light intensity and an alignment angle offset value of the composite waveplate based on the first matrix; and determine a second matrix that may characterize the composite waveplate based on the determined theoretical relationship between a light intensity and an alignment angle offset value of the composite waveplate and actually measured light intensity data.

Preferably, the processing unit is further configured to: determine the first matrix based on characteristic parameters of the composite waveplate, wherein the characteristic parameters of the composite waveplate include at least one of the following: number of single waveplates; material of the respective single waveplates; and thickness of the respective single waveplates; and an alignment angle design value of the composite waveplate.

Preferably, the processing unit is further configured to: construct a function relationship between matrix elements and the alignment angle offset value in the first matrix, such that each matrix element is only a function of the alignment angle offset value.

Preferably, the processing unit is further configured to determine the alignment angle offset value based on at least one wavelength to further determine a matrix element in the first matrix so as to determine the second matrix.

The present disclosure further provides a measuring system, comprising: a polarizer configured to produce a polarized light based on a light source; a polarization analyzer configured to detect the polarized light reflected from a surface of a sample; a detector configured to receive a light intensity of the polarized light from the polarization analyzer, wherein the measuring system further comprises: at least one composite waveplate that is disposed between the polarizer and the polarization analyzer along an optical path, and the measuring system is configured to: adjust the polarizer and/or the composite waveplate and/or the polarization analyzer to adjust the light intensity detected by the detector, and determine a matrix characterizing the composite waveplate based on a theoretical relationship between the light intensity and an alignment angle offset value of the composite waveplate.

Preferably, the measuring system is further configured to: determine a matrix that may characterize the composite waveplate based on a matrix characterizing a single waveplate in the composite waveplate and a coordinate transformation matrix determined by an alignment angle design value and the alignment angle offset value.

Preferably, the measuring system is further configured to: construct a correspondence relationship between a matrix element in the matrix characterizing the composite waveplate and the alignment angle offset value, such that each matrix element is only a function of the alignment angle offset value.

Preferably, the measuring system is also configured to: perform Fourier composition to the measured light intensity, and then determine a difference between the matrix characterizing the composite waveplate and/or a system coordinate system of the measuring system in an optical axis direction of a first single waveplate of the composite waveplate based on the theoretical light intensity value and a light wavelength.

According to an embodiment in a still further aspect of the present disclosure, a computer program product is provided, such that when the computer program product is executed by a computer device, any of the methods above is executed.

According to an embodiment in a yet further aspect of the present disclosure, there is provided a non-volatile computer-readable medium that comprises computer code which, when being executed, causes any of the methods above to be executed.

According to an embodiment in another aspect of the present disclosure, there is provided a computer device which comprises a memory and a processor, the memory storing computer code, and the processor being configured to execute any of the methods above by executing the computer code.

The technical solution of the present disclosure may greatly reduce the amount of unknown numbers when calibrating a composite waveplate or a measuring system, thereby lowering the difficulty of calibration and improving the precision of calibration.

Various aspects of the present disclosure will become much clearer through illustration of the preferred embodiments below.

BRIEF DESCRIPTION OF THE DRAWINGS

Other features, objectives and advantages of the present disclosure will become more apparent through reading the detailed depiction of the non-limiting embodiments with reference to the accompanying drawings.

In the drawings, same or similar reference numerals indicate the same or similar apparatus (module) or step throughout different drawings.

DETAILED DESCRIPTION

Figure 1:
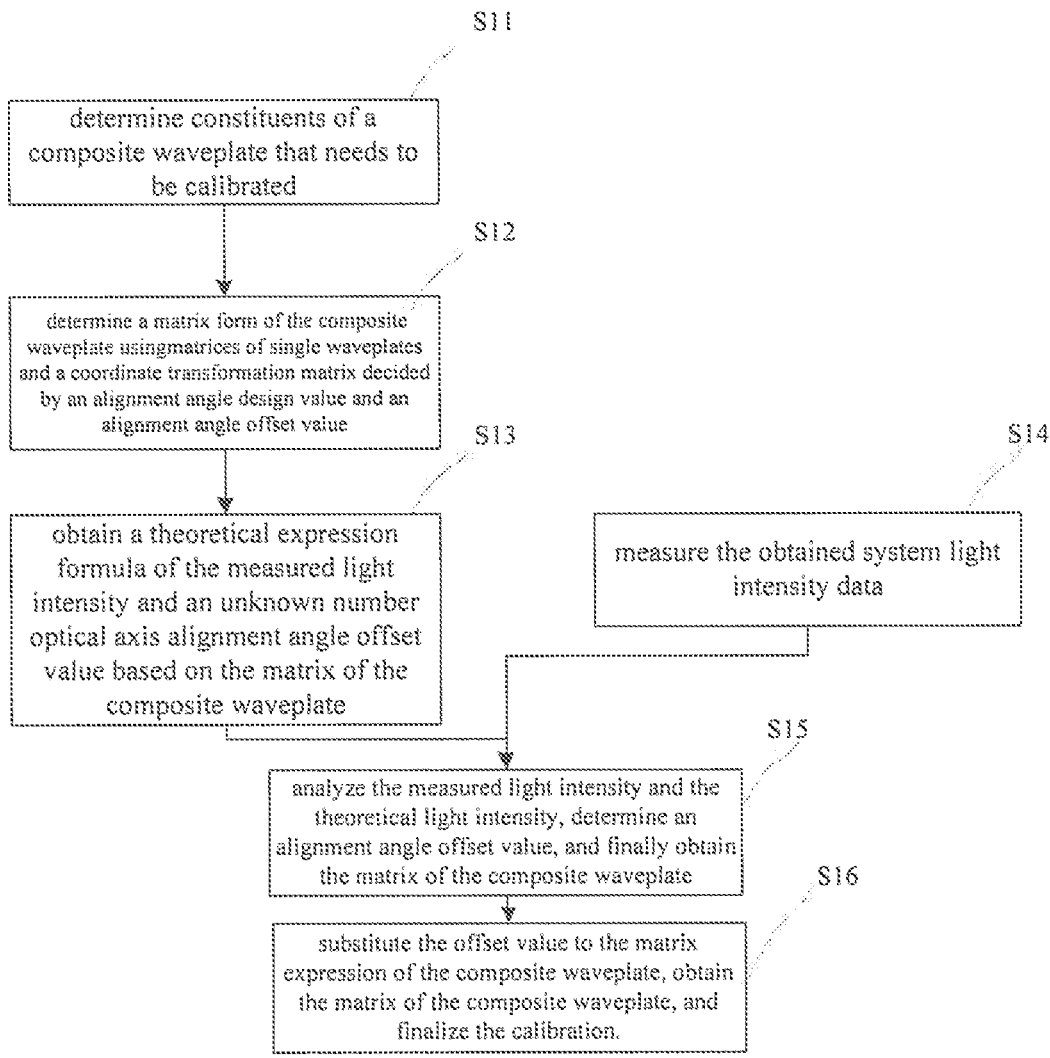
FIG. 1 is a flow diagram of a calibrating method according to an embodiment of the present disclosure.
Figure 2:
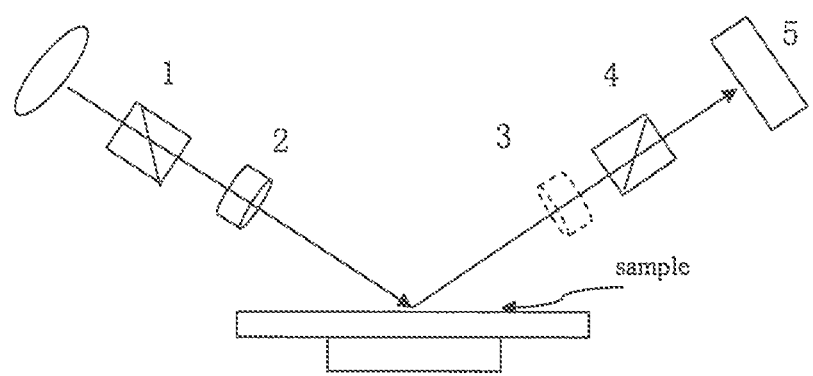
FIG. 2 is an architecture diagram of a measuring system using a composite waveplate according to an embodiment of the present disclosure.

Hereinafter, the preferred embodiments will be described in detail with reference to the accompanying drawings constituting part of the present disclosure. The accompanying drawings exemplarily show specific embodiments that may implement the present disclosure. The exemplary embodiments are not intended to exhaust all embodiments of the present disclosure. It may be understood that without departing from the scope of the present disclosure, other embodiments may be exploited or structural or logical amendments may be made. Therefore, the specific description below is not limitative, and the scope of the present disclosure is limited by the appended claims.

The "computer device" (or referred to as "computer") in the context refers to a smart electronic device that may execute a pre-processing process such as a numerical computation and/or a logic computation by executing a predetermined program or instruction, which may comprise a processor and a memory, wherein the processor executes a pre-stored program instruction in the memory to execute a predetermined processing process; or the predetermined processing process is executed by hardware such as ASIC, FPGA, and DSP, or implemented by a combination of the processor and the hardware. The computer device includes, but not limited to, a server, a personal computer, a laptop, a tablet computer, and a smart phone, etc.

An objective of the present disclosure is to provide a calibrating method for a composite waveplate in consideration of an optical axis alignment degree offset of an achromatic composite waveplate, which makes the calibration easier and more precise by reducing the unknown amount of the calibration.

Without considering a specific form of the achromatic composite waveplate, which is only regarded as a complete individual waveplate, in the case of existence of an optical axis alignment offset, a Mueller matrix of the composite waveplate may be expressed as:

$$M_C = \begin{bmatrix} 1 & 0 & 0 & 0 \\ 0 & m_{22} & m_{23} & m_{24} \\ 0 & m_{32} & m_{33} & m_{34} \\ 0 & m_{42} & m_{43} & m_{44} \end{bmatrix} \quad (1)$$

Correspondingly, calibrating the waveplate is to obtain the unknown 9 Mueller matrix elements ($m_{22}$~$m_4$), each matrix element being a function of a wavelength, each wavelength corresponding to a matrix (i.e., 9 unknown numbers). That is, when the work wavelength scope is very broad (having N wavelengths), the waveplate calibration has 9N calibrated unknown numbers.

In a Mueller measuring system, a general calibration adopts a standard unknown sample, the waveplate is regarded as an unknown amount; light is irradiated to the sample through a polarization producer and then enters a polarization detector; finally, it is detected by the detector, thereby obtaining a light intensity under each wavelength. After the forms of the Mueller matrixes of respective elements on the light path are determined, an expression for an association between the theoretically measured light intensity and the Mueller matrix element for the element in the light path may be obtained. When matrix elements other than the waveplate are known, it is determined that the light intensity measured under the wavelength is a function of the waveplate matrix element I=f($m_{22}$ ... $m_{44}$). By mathematic fitting analysis of the actually measured data with a theoretical formula, the unknown matrix elements of the waveplate are obtained. The formulae under each wavelength are the same, but the numerical values are different. By individually computing the data under each wavelength, the numerical value of the matrix elements of the waveplate corresponding to this wavelength is obtained.

It is apparent that a first drawback of this calibration is that there are relatively more unknown amounts that need to be calibrated, such that the system usually cannot calibrate all unknown amounts simultaneously. Besides, the mathematical fitting analysis is performed once under one wavelength, which not only has a large computation capacity, and the information available for computation is relatively less, while the unknown amounts are relatively many, such that the accuracy and precision of each individual unknown amount can hardly be guaranteed.

To address the above issue, the present disclosure provides an improved calibrating method: not regarding the achromatic composite waveplate as an individual entirety, but performing analysis from its constituent structure and characteristics, to first obtain its own matrix expression form (i.e., a first matrix), and then reducing unknown amounts based on the first matrix, thereby simplifying the calibration method.

A calibrating method for a composite waveplate according to an embodiment of the present disclosure comprises: A. determining a first matrix characterizing the composite waveplate, the first matrix including at least one unknown number; B. determining a theoretical relationship between a light intensity and an alignment angle offset value of the composite waveplate based on the first matrix; C. calibrating based on the theoretical relationship between a light intensity and an alignment angle offset value of the composite waveplate determined in step (B) and actually measured light intensity data to obtain a second matrix that may characterize the composite waveplate and does not contain the unknown number.

An achromatic composite waveplate is combined by two or more single waveplates of the same or different materials with optical axes formed into a certain angle. To illustrate the principle, the present embodiment takes a composite waveplate combined by two single waveplates of different materials with the optical axes being perpendicular to each other. It may be understood that the method provided by the present disclosure may also be suitable for achromatic composite waveplates of different materials, different numbers of plates, and with different optical axis alignment angles.

FIG. 1 is a flow diagram of a calibrating method according to an embodiment of the present disclosure.

Step S11: determining constituents of a composite waveplate that needs to be calibrated;

Because the achromatic composite waveplate is formed by combination of a plurality of single waveplates, while the Mueller matrix form of the single waveplate is definite; therefore, it is needed to first determine the matrix forms of the single waveplates and then determine the matrix form of the composite waveplate.

Step S12: determining a matrix form of the composite waveplate using matrices of single waveplates and a coordinate transformation matrix decided by an alignment angle design value and an alignment angle offset value.

In this step, the matrix form of the composite waveplate is determined based on characteristic parameters of the single waveplates (e.g., the number of single waveplates, materials, and thicknesses of the single waveplates) in conjunction with the coordinate transformation matrix between the alignment angle design value and the alignment angle offset value.

Step S13: obtaining a theoretical expression formula of the measured light intensity and an unknown number optical axis alignment angle offset value based on the matrix of the composite waveplate.

In this step, a theoretical function relationship between the matrix elements in the first matrix and the alignment angle offset value is constructed, such that each matrix element corresponds to the alignment angle offset value.

Step S14: measuring the obtained system light intensity data

In this step, the measurement is performed using existing waveplates and other optical components (e.g., a polarization analyzer, a polarization tester, etc.).

Step S15: analyzing the measured light intensity and the theoretical light intensity, determining an alignment angle offset value, and finally obtaining the matrix of the composite waveplate.

In this step, the theoretical expression of the light intensity and the actual measured data are subjected to mathematical fitting analysis, obtaining an amount that needs to be calibrated, the optical axis alignment angle offset value, and then in Step S16 the offset value is substituted in the expression to obtain the matrix expression of the composite waveplate, obtaining the matrix of the composite waveplate, thereby completing the calibration.

Hereinafter, the embodiments of the present disclosure will be illustrated in detail.

Expression (2) is a Mueller matrix of a single waveplate, where $\Delta$ represents a phase delay produced thereby, which is a function of wavelength:

$$M_C = \begin{bmatrix} 1 & 0 & 0 & 0 \\ 0 & 1 & 0 & 0 \\ 0 & 0 & \cos\Delta & \sin\Delta \\ 0 & 0 & -\sin\Delta & \cos\Delta \end{bmatrix} \quad (2)$$

When the material and thickness of the waveplate are known, the produced phase delay is:

$$\Delta(\lambda) = \frac{2\pi}{\lambda}[n_o(\lambda) - n_e(\lambda)]d \quad (3)$$

where $n_o$ and $n_e$ are refractive indexes of a dual-refractive material parallel to an optical axis direction and vertical to the optical axis direction, respectively, and d is a thickness of the waveplate.

A composite waveplate formed by a combination of two waveplates, with the optical axes being vertically aligned (i.e., at 90 degrees) and the optical axis direction of the first waveplate being the system coordinate system direction, has a Mueller matrix of:

$$M_{cf} = R(-\theta)M_{C_2}R(\theta)M_{C_1}$$

where the matrices of the two single waveplates are respectively:

$$M_{C_1} = \begin{bmatrix} 1 & 0 & 0 & 0 \\ 0 & 1 & 0 & 0 \\ 0 & 0 & \cos\Delta_1 & \sin\Delta_1 \\ 0 & 0 & -\sin\Delta_1 & \cos\Delta_1 \end{bmatrix}, M_{C_2} = \begin{bmatrix} 1 & 0 & 0 & 0 \\ 0 & 1 & 0 & 0 \\ 0 & 0 & \cos\Delta_2 & \sin\Delta_2 \\ 0 & 0 & -\sin\Delta_2 & \cos\Delta_2 \end{bmatrix}$$

where, $$\Delta_1(\lambda) = \frac{2\pi}{\lambda}[n_{o_1}(\lambda) - n_{e_1}(\lambda)]d_1, \Delta_2(\lambda) = \frac{2\pi}{\lambda}[n_{o_2}(\lambda) - n_{e_2}(\lambda)]d_2$$

$no_1, ne_1$ and $no_2, ne_2$ are refractive indexes of the two materials, which are a function of wavelength; therefore, the Mueller matrix of a single waveplate has a matrix at each wavelength, each wavelength corresponding to a different matrix.

Wherein the matrix $R(\theta)$ is a rotation matrix between the optical element coordinate axis and the system coordinate axis, expressed as:

$$R(\theta) = \begin{bmatrix} 1 & 0 & 0 & 0 \\ 0 & \cos2\theta & \sin2\theta & 0 \\ 0 & -\sin2\theta & \cos2\theta & 0 \\ 0 & 0 & 0 & 1 \end{bmatrix}$$

With the optical axis direction of the first single waveplate is the system coordinate system direction, the two waveplate optical axes are vertical to each other; then $\theta=90°$.

$$M_{cf} = \quad (4)$$

$$R(-90)M_{C_2}R(90)M_{C_1} = \begin{bmatrix} 1 & 0 & 0 & 0 \\ 0 & -1 & 0 & 0 \\ 0 & 0 & -1 & 0 \\ 0 & 0 & 0 & 1 \end{bmatrix}\begin{bmatrix} 1 & 0 & 0 & 0 \\ 0 & 1 & 0 & 0 \\ 0 & 0 & \cos\Delta_1 & \sin\Delta_1 \\ 0 & 0 & -\sin\Delta_1 & \cos\Delta_1 \end{bmatrix}$$

$$\begin{bmatrix} 1 & 0 & 0 & 0 \\ 0 & -1 & 0 & 0 \\ 0 & 0 & -1 & 0 \\ 0 & 0 & 0 & 1 \end{bmatrix}\begin{bmatrix} 1 & 0 & 0 & 0 \\ 0 & 1 & 0 & 0 \\ 0 & 0 & \cos\Delta_2 & \sin\Delta_2 \\ 0 & 0 & -\sin\Delta_2 & \cos\Delta_2 \end{bmatrix} =$$

$$\begin{bmatrix} 1 & 0 & 0 & 0 \\ 0 & 1 & 0 & 0 \\ 0 & 0 & \cos(\Delta_1 - \Delta_2) & \sin(\Delta_1 - \Delta_2) \\ 0 & 0 & -\sin(\Delta_1 - \Delta_2) & \cos(\Delta_1 - \Delta_2) \end{bmatrix}$$

When the optical axis alignment degree is offset by 90 degrees, i.e., there exists a minor alignment angle offset value $C_\Delta$, the matrix of the composite waveplate is changed as:

$$M_{cf} = R(-90 - C_\Delta)M_{C_2}R(90 + C_\Delta)M_{C_1} = \quad (5)$$

-continued $$\begin{bmatrix} 1 & 0 & 0 & 0 \\ 0 & \frac{1+\cos\Delta_2}{2} + \frac{(1-\cos\Delta_2)\cos4C_\Delta}{2} & \frac{\sin4C_\Delta\cos\Delta_1(1-\cos\Delta_2)}{2} - \sin2C_\Delta\sin\Delta_1\sin\Delta_2 & \frac{\sin4C_\Delta\sin\Delta_1(1-\cos\Delta_2)}{2} + \sin2C_\Delta\cos\Delta_1\sin\Delta_2 \\ 0 & \frac{\sin4C_\Delta(1-\cos\Delta_2)}{2} & \frac{(1+\cos4C_\Delta(\cos\Delta_2-1)+\cos\Delta_2)}{2}\cos\Delta_1 + \cos2C_\Delta\sin\Delta_1\sin\Delta_2 & \frac{(1+\cos4C_\Delta(\cos\Delta_2-1)+\cos\Delta_2)}{2}\sin\Delta_1 - \cos2C_\Delta\cos\Delta_1\sin\Delta_2 \\ & & \cos2C_\Delta\sin\Delta_2\cos\Delta_1 - \cos\Delta_2\sin\Delta_1 & \cos2C_\Delta\sin\Delta_2\sin\Delta_1 + \cos\Delta_2\cos\Delta_1 \\ 0 & -\sin2C_\Delta\sin\Delta_2 & & \end{bmatrix}$$

When $C_A=0$, the equation (5) will be regressed to the result of expression (4); it may be seen from equation (5) that after the optical axis has a certain offset from the designed angle, the Mueller matrix of the composite waveplate will not be an ideal matrix, and the original 0 matrix element has a numerical value, and the value of non-zero matrix element will also change. Therefore, the Mueller matrix of the composite waveplate must be precisely calibrated so as to obtain a relatively fine precision upon system measurement. If the specific form of the matrix element is not considered while the composite wavelength is regarded as an entirety, there will be 9 unknown numbers under one wavelength.

It may be seen from expression (5) that the 9 unknown amounts $m_{22} \sim m_{44}$ in expression (1) are not mutually independent, but a function of the optical axis alignment angle offset value $C_A$ and the refractive index and thickness of the waveplate material itself (the equation of $\Delta_{1,2}$ is shown in expression (3)). Apparently, when which kind of waveplate is determined, its material, refractive index, and thickness have been determined. In this way, the matrix element of the waveplate is the function of the alignment angle offset value $C_A$; but $C_A$ is not the function of the wavelength, which is the same value for all wavelengths. In this way, the unknown numbers of the whole system turn from 9N (suppose N wavelengths are measured) to 1. After the form of the matrix (5) is determined, the measured data (i.e., light intensity) and the theoretical equation are subjected to mathematical fitting analysis to obtain an unknown amount that needs to be calibrated; when deriving the theoretical equation, the matrix element of the waveplate is expressed using equation (5), and the resulting theoretical equation is the same under each wavelength; although the refractive indexes under different wavelengths are different, the numerical value of the matrix element is still different under each wavelength; however, the unknown number of the equation has only one $C_A$ irrespective of the wavelength. Therefore, data of each wavelength may be used to calibrate $C_A$; the data amount is large, but the unknown amount is small; thereby the calibration difficulty is reduced while the accuracy and precision are correspondingly enhanced. After obtaining $C_A$ through calibration, it may be substituted into equation (5) to obtain all matrix elements of the waveplate.

The example above is directed to a composite waveplate combined by two individual waveplates of different materials, with the optical axes being at 90 degrees with each other; this calibrating method is also suitable for scenarios in which the number of single waveplates in a composite waveplate increases and the optical axis design angle is any angle. Still starting from a single waveplate, a matrix expression of the composite waveplate is obtained; after the material and alignment angle are determined, each matrix element will only be a function of the alignment angle offset value. With increase of the number of waveplates, the unknown number will also increase. With one more waveplate, there will be one more alignment angle offset value unknown number, however, even in this case, the unknown numbers are reduced much compared with 9N number.

Now, the preferred embodiments of the present disclosure will be illustrated with a specific measuring system to measure and calibrate under a parallel light.

The measuring system comprises: a polarizer 1 configured to generate a polarized light based on a light source; a first composite waveplate 2 disposed between the polarizer and a sample along an optical path; a polarization analyzer 4, and a detector 5 configured to receive an optical signal from the polarization analyzer.

The measuring system is configured to: adjust at least one the polarizer 1, the first composite waveplate 2, and a polarization analyzer 4 to adjust the light intensity data obtained by the detector 5, and determine a second matrix that may characterize the first composite waveplate based on a theoretical relationship between the light intensity and an alignment angle offset value of the composite waveplate.

Specifically, the measuring system is adjusted first, such that it may determine various measurement parameters of the system in a measurement state and the Mueller matrix forms of respective optical elements in the system other than the first composite waveplate; in a general Mueller matrix measuring system, the polarizer has a very minor error amount, which thus may be regarded as an ideal element. The sample may adopt various kinds of different standard samples. The Mueller matrices of such standard samples are known, e.g., a bare silica crystal plate, or a $S_iO_2$ film of a given thickness.

The light of the light source S enters the first composite waveplate 2 of the incident end via the polarizer 1, irradiated the sample, reflected into the polarization analyzer 4 of the exit end through the sample, and then entering the detector 5. The polarizer 1 and the first composite waveplate 2 form the polarization generator of the incident end, and the polarization analyzer 4 is a polarization detector.

The work modes (the modes of measuring the light intensity) of the system may be plural. For example, rotating the polarization analyzer 4 to measure, or rotating the polarizer 1 or adding one composite waveplate 3 (expressed in dotted lines, which may be a waveplate that has been calibrated or a waveplate that needs to be calibrated), rotating any waveplate or simultaneously rotating two waveplates (a certain ratio exists between the rotation speeds of the waveplates), etc. If the composite waveplate is regarded as a whole, in order to calibrate the unknown 9 matrix elements (under one wavelength), it is required that to calibrate as many amounts as possible by calibration with joint measurements of all of the plurality of working modes. Now, there is only one unknown amount $C_A$ (in the case of two composite waveplates that need to be calibrated, there are two unknown amounts $C\Delta_{1,2}$, because the alignment offsets of the two waveplates are different), it is only required to adopt any kind of working mode. We use the working mode of rotating the polarizer as an example.

Rotating the polarization analyzer to obtain the light intensity measured from experiment. Theoretically, the theoretical equation between the light intensity and the waveplate Mueller matrix element is derived:

$$S=R(-A)M_AR(A)M_SR(-C_1)M_{Cf1}R(-C_1)R(-P)M_PR(P) \\ S_0 \quad (6)$$

Where $S_0$ is Stokes quantity of the incident light source; the Stokes quantity is a quantity that describes a polarization feature of light, a 4×1 vector, with the first element being light intensity. S denotes the Stokes quantity when the light passes the system, whose first quantity S(1) is the light intensity that may be detected. $M_P, M_A, M_S$ are Mueller matrixes of the polarizer, polarization analyzer, and sample, respectively; $M_{Cf1}$ is the waveplate matrix of the incident end, R matrix is the rotation and transformation matrix of the coordinate axis and the system coordinate axis of the element, wherein P and A are included angles between the optical axes of the polarizer and the polarization analyzer with the system coordinate axis, respectively; $C_1$ is the included angle between the first single waveplate of the two single waveplates of the composite waveplate and the system coordinate axis; when deriving the equation (5), it is based on the optical axis direction of the first single waveplate of the composite waveplate; in system, a hardware installation and debugging requirement requires that this direction should be consistent with the coordinate axis direction of the system; but a certain deviation also exists. This deviation is $C_1$. In order to calibrate the entire system more accurately, C1 is reckoned herein, which is also a number independent of wavelength and may be used as a quantity for joint calibration.

To obtain the first element of S, i.e., the theoretically measurable light intensity, when the angle P of the polarizer 1 is given, the polarization analyzer 4 is rotated to measure. This light intensity is a function of the calibration quantity of the composite waveplate and the time. Equation (5) is substituted into the matrix of the waveplate, i.e., the form of the light intensity is expressed below:

$$I=I(t)=S[1]=I_0(1+\alpha_2(C_\Delta,C_1)\cos(2\omega t)+\beta_2(C_\Delta,C_1)\sin(2\omega t)) \quad (7)$$

where ω is the angular speed of rotation of the polarization analyzer, and $\alpha_2(C_\Delta,C_1,),\beta_2(C_\Delta,C_1,)$ are function expressions of quantities to be calibrated.

The measured light intensities are subject to Fourier decomposition to obtain experimental α2,β2; arithmetic fitting is performed to the function expressions of their theoretical values, obtaining $C_\Delta,C_1$ that need to be calibrated, i.e., obtaining the matrixes of waveplates that need to be calibrated. When making arithmetic fitting, data of one wavelength may be resolved. In order to enhance the precision, the data of a plurality of wavelengths may be employed to fit to obtain the quantity that needs to be calibrated.

The present disclosure further provides a calibrating apparatus for a composite waveplate, comprising: a detecting unit configured to receive or detect a measured light intensity; a processing unit configured to: determine a first matrix characterizing the composite waveplate, the first matrix including at least one unknown number; determine a theoretical relationship between the light intensity and an alignment angle offset value of the composite waveplate based on the first matrix; and determine a second matrix that may characterize the composite waveplate based on the determined theoretical relationship between a light intensity and an alignment angle offset value of the composite waveplate and actually measured light intensity data.

Preferably, the processing unit is further configured to: determine the first matrix based on characteristic parameters of the composite waveplate, wherein the characteristic parameters of the composite waveplate include at least one of the following: number of single waveplates; material of the respective single waveplates; and thickness of the respective single waveplates; and an alignment angle design value of the composite waveplate.

Preferably, the processing unit is further configured to: construct a function relationship between matrix elements and the alignment angle offset value in the first matrix, such that each matrix element is only a function of the alignment angle offset value.

Preferably, the processing unit is further configured to: determine the alignment angle offset value based on at least one wavelength to further determine a matrix element in the first matrix so as to determine the second matrix. It may be understood that the more wavelengths to use, the more accurate the determined data.

To those skilled in the art, it is apparent that the present disclosure is not limited to the details of the above exemplary embodiments, and the present disclosure may be implemented with other embodiments without departing from the spirit or basic features of the present disclosure. Thus, in any way, the embodiments should be regarded as exemplary, not limitative. Besides, it is apparent that the term "comprise" does not exclude other units or steps, and singularity does not exclude plurality. A plurality of units or modules stated in a system claim may also be implemented by a single unit or module through software or hardware. Terms such as the first and the second are used to indicate names, but do not indicate any particular sequence. It should be noted that the present disclosure (e.g., the calibrating method in the context) may be implemented in software and/or or a combination of software and hardware. For example, each module of the present disclosure may be implemented by an application-specific integrated circuit (ASIC) or any other similar hardware device. In one embodiment, the software program of the present disclosure may be executed through a processor to implement the steps or functions as mentioned above. Likewise, the software program (including relevant data structure) of the present disclosure may be stored in a computer readable recording medium, e.g., RAM memory, magnetic or optic driver or soft floppy or similar devices. Additionally, some steps or functions of the present disclosure may be implemented by hardware, for example, a circuit cooperating with the processor so as to implement various steps of functions.

In addition, part of the present disclosure may be applied as a computer program product, e.g., a computer program instruction which, when executed by the computer, may invoke or provide the method and/or technical solution according to the present disclosure through operation of the computer, while the program instruction that invokes the method of the present disclosure may be stored in the fixed or movable recording medium, and/or transmitted by broadcasting or the data stream in other signal carrying medium, and/or stored on the work memory of the computer system running according to the program instruction. Here, an embodiment according to the present disclosure comprises an apparatus, the apparatus comprising a memory for storing the computer program instructions and a processor for executing the program instructions, wherein when the computer program instructions are executed by the processor, the apparatus is triggered to run the method and/or technical solution of the plurality of embodiments according to the present disclosure.

What is claimed is:

1. A calibrating method for a composite waveplate, comprising:
   A. determining a first matrix characterizing the composite waveplate, the first matrix including at least one unknown number;
   B. determining a theoretical relationship between a light intensity and an alignment angle offset value of the composite waveplate based on the first matrix; and
   C. calibrating based on the theoretical relationship between the light intensity and the alignment angle offset value of the composite waveplate determined in step (B) and actually measured light intensity data to obtain a second matrix that characterizes the composite waveplate and does not contain the unknown number.

2. The method according to claim 1, characterized in that the at least one unknown number includes the alignment angle offset value.

3. The method according to claim 1, characterized in that the step A further comprises:
   determining the first matrix based on a third matrix characterizing a single waveplate in the composite waveplate and a coordinate transformation matrix determined by an alignment angle design value and the alignment angle offset value.

4. The method according to claim 3, characterized in that the step A further comprises:
   determining the third matrix based on characteristic parameters of the single waveplate, wherein the characteristic parameters include at least one of the following:
   number of the single waveplates;
   materials of the respective single waveplates; and
   thickness of the respective single waveplates.

5. The method according to claim 1, characterized in that the step B further comprises:
   constructing a function relationship between matrix elements and the alignment angle offset value in the first matrix, such that each matrix element corresponds to the alignment angle offset value.

6. The method according to claim 1, characterized in that the step C further comprises:
   determining the alignment angle offset value based on at least one wavelength to further determine an unknown matrix element in the first matrix so as to determine the second matrix.

7. A calibrating apparatus for a composite waveplate, comprising:
   a detecting unit configured to receive or detect a measured light intensity;
   a processing unit configured to:
      determine a first matrix characterizing the composite waveplate, the first matrix including at least one unknown number;
      determine a theoretical relationship between the light intensity and an alignment angle offset value of the composite waveplate based on the first matrix; and
      determine a second matrix that characterizes the composite waveplate based on the determined theoretical relationship between the light intensity and the alignment angle offset value of the composite waveplate and actually measured light intensity data.

8. The apparatus according to claim 7, characterized in that the processing unit is further configured to:
   determine the first matrix based on characteristic parameters of the composite waveplate, wherein the characteristic parameters of the composite waveplate include at least one of the following:
   number of single waveplates;
   material of the respective single waveplates;
   thickness of the respective single waveplates; and
   an alignment angle design value of the composite waveplate.

9. The apparatus according to claim 7, characterized in that the processing unit is further configured to:
   construct a function relationship between matrix elements and the alignment angle offset value in the first matrix, such that each matrix element is only a function of the alignment angle offset value.

10. The apparatus according to claim 7, characterized in that the processing unit is further configured to:
    determining the alignment angle offset value based on at least one wavelength to further determine a matrix element in the first matrix so as to determine the second matrix.

11. A measuring system, comprising:
    a polarizer configured to produce a polarized light based on a light source;
    a polarization analyzer configured to detect the polarized light reflected from a surface of a sample; and
    a detector configured to receive a light intensity of the polarized light from the polarization analyzer;
    wherein the measuring system further comprises:
    at least one composite waveplate that is disposed between the polarizer and the polarization analyzer along an optical path, and the measuring system is configured to:
    adjust the polarizer and/or the composite waveplate and/or the polarization analyzer to adjust the light intensity detected by the detector, and determine a matrix characterizing the composite waveplate based on a theoretical relationship between the light intensity and an alignment angle offset value of the composite waveplate.

12. The measuring system according to claim 11, characterized in that the measuring system is further configured to:
    determine a matrix that may characterize the composite waveplate based on a matrix characterizing a single waveplate in the composite waveplate and a coordinate transformation matrix determined by an alignment angle design value and the alignment angle offset value.

13. The measuring system according to claim 12, characterized in that the measuring system is further configured to:
    construct a correspondence relationship between a matrix element in the matrix characterizing the composite waveplate and the alignment angle offset value, such that each matrix element is only a function of the alignment angle offset value.

14. The measuring system according to claim 11, characterized in that the measuring system is further configured to:
    perform Fourier composition to the measured light intensity, and then determine a difference between the matrix characterizing the composite waveplate and/or a system coordinate system of the measuring system in an optical axis direction of a first single waveplate of the composite waveplate based on the theoretical light intensity value and a light wavelength.

15. A computer program product, such that when the computer program product is executed by a computer device, a calibrating method for a composite waveplate is executed, the method comprising:
   A. determining a first matrix characterizing the composite waveplate, the first matrix including at least one unknown number;
   B. determining a theoretical relationship between a light intensity and an alignment angle offset value of the composite waveplate based on the first matrix; and
   C. calibrating based on the theoretical relationship between the light intensity and the alignment angle offset value of the composite waveplate determined in step (B) and actually measured light intensity data to obtain a second matrix that characterizes the composite waveplate and does not contain the unknown number.

16. A non-volatile computer-readable medium, including computer code which, when being executed by the computer code, causes a calibrating method for a composite waveplate to be executed,
   A. determining a first matrix characterizing the composite waveplate, the first matrix including at least one unknown number;
   B. determining a theoretical relationship between a light intensity and an alignment angle offset value of the composite waveplate based on the first matrix; and
   C. calibrating based on the theoretical relationship between the light intensity and the alignment angle offset value of the composite waveplate determined in step (B) and actually measured light intensity data to obtain a second matrix that characterizes the composite waveplate and does not contain the unknown number.

17. A computer device which comprises a memory and a processor, the memory storing computer code, and the processor being configured to execute a calibrating method for a composite waveplate by executing the computer code, the method comprising:
   A, determining a first matrix characterizing the composite waveplate, the first matrix including at least one unknown number;
   B. determining a theoretical relationship between a light intensity and an alignment angle offset value of the composite waveplate based on the first matrix;
   and C. calibrating based on the theoretic al relationship between the light intensity and the alignment angle offset value of the composite waveplate determined in step (B) and actually measured light intensity data to obtain a second matrix that characterizes the composite waveplate and does not contain the unknown number.

\* \* \* \* \*